United States Patent
Baird et al.

(10) Patent No.: US 9,079,022 B2
(45) Date of Patent: *Jul. 14, 2015

(54) LED BASED PHOTOTHERAPY DEVICE FOR PHOTO-REJUVENATION OF CELLS

(75) Inventors: Craig Baird, Vancouver (CA); Stan Stanbridge, Costa Mesa, CA (US)

(73) Assignee: LED Intellectual Properties, LLC, Irvine, CA (US)

( * ) Notice: Subject to any disclaimer, the term of this patent is extended or adjusted under 35 U.S.C. 154(b) by 1247 days.

This patent is subject to a terminal disclaimer.

(21) Appl. No.: 12/205,199

(22) Filed: Sep. 5, 2008

(65) Prior Publication Data

US 2009/0088824 A1   Apr. 2, 2009

Related U.S. Application Data

(60) Provisional application No. 60/995,479, filed on Sep. 27, 2007, provisional application No. 60/995,696, filed on Sep. 28, 2007, provisional application No. 60/995,703, filed on Sep. 28, 2007, provisional application No. 60/995,705, filed on Sep. 28, 2007.

(51) Int. Cl.
*A61N 5/06* (2006.01)

(52) U.S. Cl.
CPC ....... *A61N 5/0616* (2013.01); *A61N 2005/0644* (2013.01); *A61N 2005/0652* (2013.01)

(58) Field of Classification Search
CPC .............. A61N 2005/0644; A61N 2005/0652; A61N 2005/0059; A61N 2005/0662
USPC ................... 607/88, 89, 90, 91, 94; 606/2, 13
See application file for complete search history.

(56) References Cited

U.S. PATENT DOCUMENTS

| | | | | |
|---|---|---|---|---|
| 4,930,504 A | * | 6/1990 | Diamantopoulos et al. | 607/88 |
| 5,259,380 A | * | 11/1993 | Mendes et al. | 607/115 |
| 5,278,432 A | * | 1/1994 | Ignatius et al. | 257/88 |
| 5,358,503 A | * | 10/1994 | Bertwell et al. | 606/27 |
| 5,698,866 A | * | 12/1997 | Doiron et al. | 257/99 |
| 5,728,090 A | * | 3/1998 | Martin et al. | 606/3 |
| 6,471,716 B1 | * | 10/2002 | Pecukonis | 607/89 |
| 6,596,016 B1 | * | 7/2003 | Vreman et al. | 607/88 |
| 6,602,275 B1 | | 8/2003 | Sullivan | |
| 6,645,230 B2 | * | 11/2003 | Whitehurst | 607/88 |
| 6,828,576 B2 | | 12/2004 | Spivak | |
| 7,081,128 B2 | | 7/2006 | Hart et al. | |
| 7,125,416 B2 | * | 10/2006 | Kent et al. | 607/88 |

(Continued)

FOREIGN PATENT DOCUMENTS

WO   WO 2004105586 A2 * 12/2004
WO   WO 2005086846 A2 *  9/2005

*Primary Examiner* — Cris L Rodriguez
*Assistant Examiner* — Matthew Saunders
(74) *Attorney, Agent, or Firm* — Price Heneveld LLP

(57) ABSTRACT

An improvement in a light therapy device including multiple light-emitting diodes (LEDs) positioned in a handheld portable device is disclosed. Where the housing and the LEDs are configured to have direct contact with the skin or tissue of the user without any intermediary materials, and light the surface and underlying layers of tissue for photodynamic stimulation of the cells. Two iterations of the device utilize light known to have a bactericidal effect in the case or acne or Rosacea. The devices are fabricated from an injection molded plastic housing. The housing contains an arrangement of 36-72 LEDs on a circuit board in an arrangement to provide even lighting over the skin or tissue surface.

16 Claims, 6 Drawing Sheets

(56) References Cited

U.S. PATENT DOCUMENTS

| | | | |
|---|---|---|---|
| 7,131,990 B2* | 11/2006 | Bansal et al. | 607/90 |
| 7,175,587 B2 | 2/2007 | Gorden et al. | |
| 7,204,846 B2* | 4/2007 | Suzuki | 607/88 |
| 7,267,673 B2 | 9/2007 | Pilcher et al. | |
| 2003/0187486 A1* | 10/2003 | Savage et al. | 607/89 |
| 2003/0233138 A1* | 12/2003 | Spooner | 607/93 |
| 2004/0030370 A1* | 2/2004 | Lytle | 607/89 |
| 2004/0147984 A1* | 7/2004 | Altshuler et al. | 607/88 |
| 2004/0193234 A1* | 9/2004 | Butler | 607/88 |
| 2004/0230259 A1* | 11/2004 | Di Matteo | 607/88 |
| 2005/0085875 A1* | 4/2005 | Van Zuylen | 607/88 |
| 2006/0020308 A1 | 1/2006 | Muldner | |
| 2006/0030908 A1 | 2/2006 | Powell | |
| 2006/0212025 A1 | 9/2006 | McDaniel | |
| 2006/0287696 A1* | 12/2006 | Wright et al. | 607/88 |
| 2007/0032843 A1* | 2/2007 | Hsu | 607/88 |
| 2007/0106347 A1* | 5/2007 | Lin | 607/88 |
| 2008/0103563 A1 | 5/2008 | Powell et al. | |

* cited by examiner

| Purpose | LED IDENTIFER | | | | |
|---|---|---|---|---|---|
| | ○ | ● | ⊖ | ⊞ | ⊘ |
| | 21 | 22 | 23 | 24 | 25 |
| Skin Rejuvenation | 850 | 660 | 630 | 605 | 605 |
| Reduction of Rosacea | 850 | 660 | 630 | 465 | 605 |
| Reduction of Acne | 850 | 660 | 465 | 460 | 660 |
| Therapeutic Application | 630 | 660 | 850 | 940 | 660 |

LED BASED PHOTOTHERAPY DEVICE FOR PHOTO-REJUVENATION OF CELLS

CROSS REFERENCE TO RELATED APPLICATION

This application claims priority to Provisional Application 60/995,479 filed Sep. 27, 2007, Provisional Application 60/995,696 filed Sep. 28, 2007, Provisional Application 60/995,703 filed Sep. 28, 2007 and Provisional Application 60/995,705 filed Sep. 28, 2007.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to light therapy and more particularly to a therapy system utilizing light emitting diodes as a source of bio-stimulative non-coherent non-monochromatic light.

This invention relates to improvements in medical devices for topical photodynamic therapy (POT) treatment to patient's, and particularly to a rigid surface (circuit board) containing light emitting diodes (LEDs) as a source of bio-stimulative non-coherent non-monochromatic light, which is placed in contact or in close proximity with the patient's skin or tissue, and a method for making that apparatus.

Description of Related Art Including Information Disclosed Under 37 CFR 1.97 and 1.98.

Several products have been available. Exemplary examples of patents covering these products are disclosed herein.

Nonmonochromatic light as defined wavelengths has produced beneficial bio-stimulative effects and has been known to trigger specific biological functions, such as, increased rate of metabolism, photo-repair and cell division. Stimulation occurred, however, With light emitted in specific wavelengths.

While the exact mechanism by which the beneficial bio-stimulative effects have been achieved is not precisely known, several theories have been put forth. It has been put forth. It has been suggested that non-monochromatic light emitted in the range of 460 to 940 nm penetrates body tissue and is absorbed, reflected and scattered to excite molecules within cells and tissue to thereby accelerate repair and regeneration. It is known however that light in the range of 460 nm TO 465 nm has a bactericidal effect thereby relieving the appearance of bacteria induced acne.

A further theory suggested that different cells had different photoreceptors, which responded to only particular wavelengths of light. This theory supported the phenomenon that the application of only certain wavelengths of light resulted in bio-stimulative effects and the resulting stimulation of the dermis and an increase of collagen and elastin production.

Light therapy has utilized lasers with relatively low power and bio-stimulative treatment utilizing lasers has been referred to as "soft" laser therapy. In such applications, low level laser energy radiation has been successfully employed to stimulate wound healing and treatment of musculoskeletal disorders and skin ulcers.

It has been previously theorized that the properties of laser radiation, which resulted in the beneficial bio-stimulative effects of soft laser therapy, were the monochromaticity and coherence of laser radiation.

It occurred to applicants that if bio-stimulative light effects could be compounded by combining into one device 4 different wavelengths of light each with known benefits, that the effects could be greater than if each wavelength was applied separately and close proximity of the LEDs were such that this promoted uniform coverage of the target area to receive all wavelengths simultaneously.

Published U.S. Patent application 2006/0020308 that was published on Jan. 26, 2006 to James Scott Muldner discloses a light therapy device heat management device. The disclosed device uses transmitted thermal energy with different colored LED's to stimulate skin. While this product uses a combination of light and heat, the heat is generated from heating pads and the heat is blown through the device to heat the skin. While this patent discloses heating along with the light therapy the heating is generated from a thermal heater as opposed to generating heat by overdriving the lighting (LED's).

Published U.S. Patent application 2008/0103563 that was published on May 1, 2008 to Steven D. Powell discloses a light therapy personal care device. The device combines light therapy with an exfoliating pad or a razor. While this invention uses light therapy there is no heating of the skin that will open pores to further improve skin condition.

U.S. Pat. No. 6,602,275 issued Aug. 5, 2003 to Jana Sullivan discloses a device and method for therapeutic treatment of living organisms. The device is a plurality of different colored LED's in combination with a heating or cooling pad. While this patent discloses heating with LED's the heating is from a separate thermal pad that is placed on the skin prior to or after the light therapy.

U.S. Pat. No. 5,358,503 issued Oct. 25, 1994 to Dale E. Bertwell et al discloses a light therapy device with LED's that are heated with resistors. The LED's conduct the heat from the resistors to the skin. While this patent discloses light therapy with heating the heating is provided with resistors and conducted through the LED's.

What is needed is a light therapy device that creates heat by overdriving the LED so the LED's generate thermal heat that is conducted onto a user's skin. The proposed device provides this solution in a handheld and mountable device.

BRIEF SUMMARY OF THE INVENTION

It is an object of the LED light therapy device to comprises a system for light therapy which utilizes non-coherent light generated by an array of conventional light emitting diodes (LEDs) which are confined within a bandwidth of 460 nm to 940 nm. The diode array is configured in a matrix to direct the light onto a diffuse area of the user without utilizing an optical system or any intermediary material. The LEDs rest directly, or in close proximity, on the user's skin.

From the foregoing, it should be apparent that it is an aspect of the present invention to provide a light therapy system of the general character described which is not subject to the limitations of single wavelength devices.

It is an object of the LED light therapy device to provide a light therapy system of the general character described which is lightweight and portable.

It is an object of the LED light therapy device to provide a light therapy system of the general character described which is well suited for relatively low cost mass production fabrication and is a still further consideration of the present invention.

It is an object of the LED light therapy device to provide a light therapy system of the general character described which is simple in operation and convenient for home use.

It is an object of the LED light therapy device to overdrive the LED's to create heat that is conducted to the skin of the user to provide heat in addition to the light therapy. In some embodiments a single resistor is used to consistently limit the current to all of the LED's and provide both even illumination and heat.

It is another object of the LED light therapy device to provide a light therapy system of the general character described, which produces beneficial bio-stimulative effects.

It is another object of the LED light therapy device to provide a light therapy method of the general character described whereby non-coherent and non-monochromatic light within a wavelength range of 460 nm to 940 nm is employed for photo-bio-stimulation.

It is still another object of the LED light therapy device to provide a light therapy method of the general character described which utilized non-coherent and non-monochromatic light emanating from conventional light emitting diodes.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

DETAILED DESCRIPTION OF THE INVENTION

Figure 1:
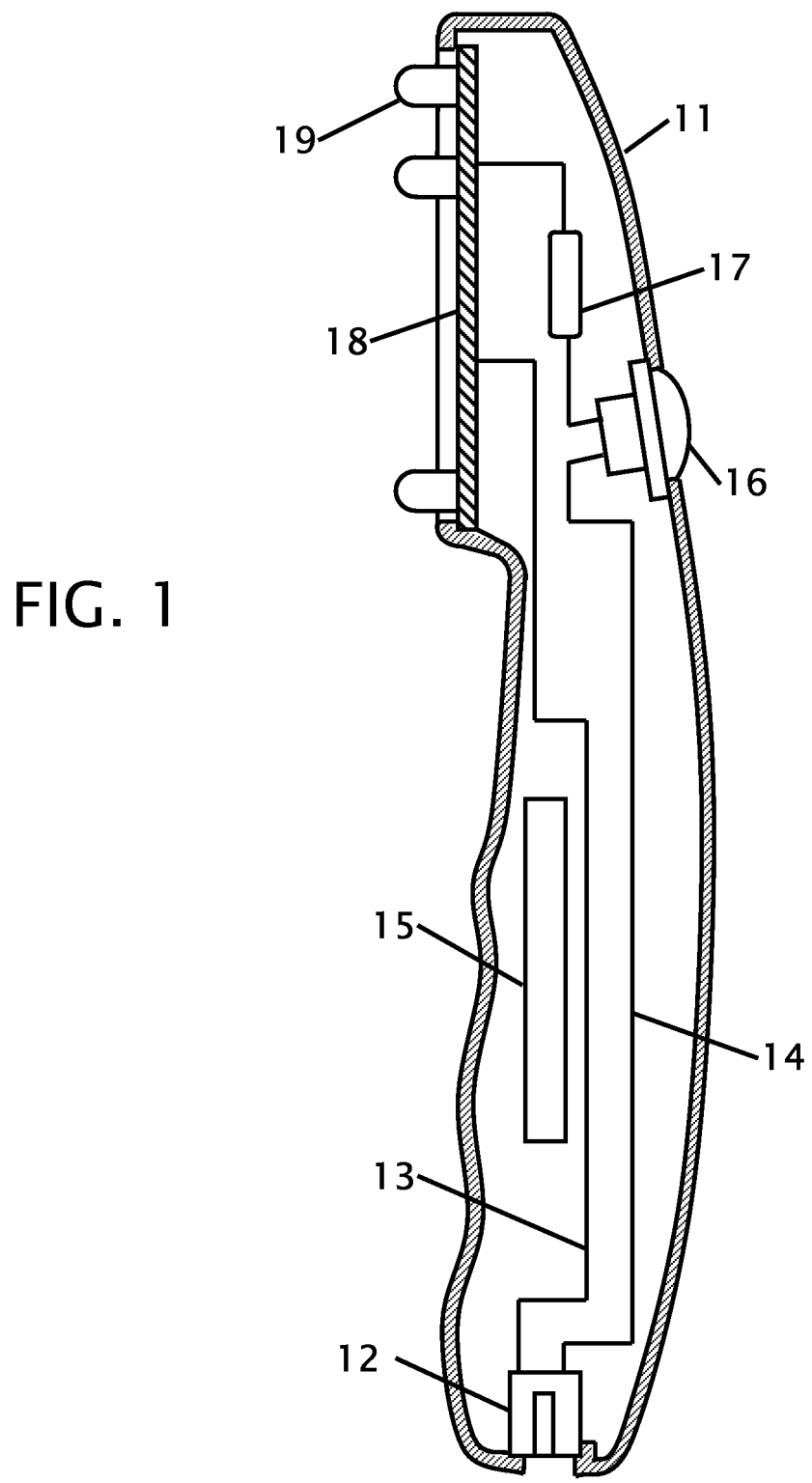
FIG. 1 shows a cross sectional view of a hand held version of the LED light therapy device.

FIG. 1 shows a cross sectional view of a hand held version of the LED light therapy device. The device includes an array of 36 to 72 light emitting diodes incorporated in 9-18 parallel circuits of 4 in a series of conventional light emitting diodes configured to emanate an even distribution of light in the following wavelengths 460 nm, 465 nm, 605 nm, 630 nm, 660 nm, 850 nm and 940 nm, depending on the designed intent of the device. The selection for the different wavelength light emitting diodes based upon the intended use is shown and described in more detail with FIGS. 5 and 6. While a particular number and array of light emitting diodes has been disclosed more or less light-emitting diodes can be used in other larger or smaller designs.

In FIG. 1 the device is enclosed in a plastic housing 11. The device is energized by an external AC to DC 9-12 volt 300-500 mA power supply through a connector 12 to a negative lead 13 and a positive lead 14 then to the on/off switch 16 and then through a current limiting resistor 17 and finally to the rigid printed circuit board 18 that holds the different wavelength light emitting diodes 19. A weight 15 is preferably placed in the handle to provide balance to the device.

FIG. 1 comprises a cross sectional view through the device including a printed circuit board 18. The output of all of the light emitting diodes 19 is directed outward at right angles, or normal, to the circuit board 18 on which they are mounted without lenses, mirrors, reflective surfaces, optical systems or any intermediary material.

Figure 2:
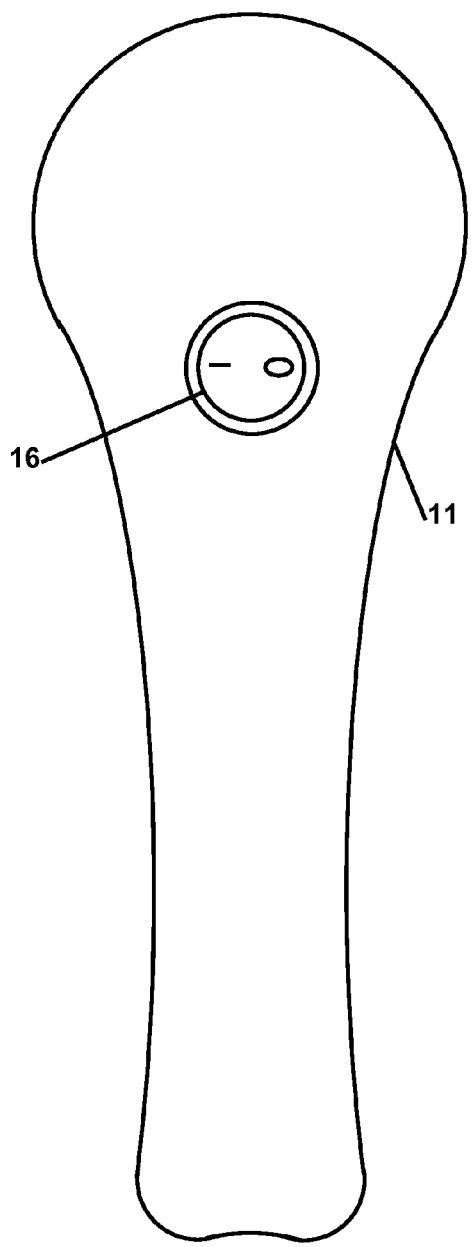
FIG. 2 is a top view of the device showing the location of the on/off power switch.
Figure 3:
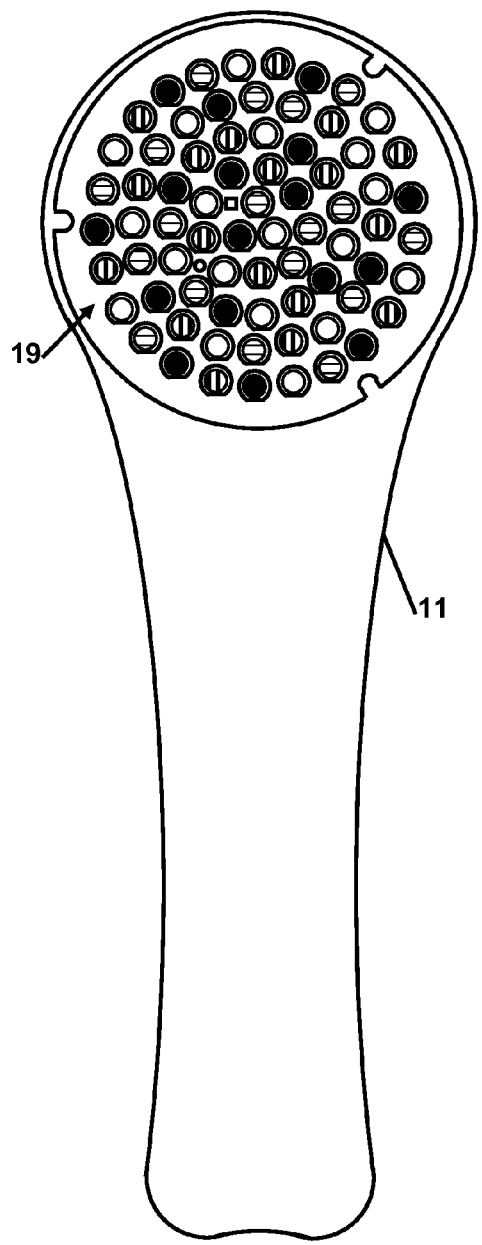
FIG. 3 is a bottom view showing an arrangement of the light emitting diodes arranged for multiple purposes.

FIG. 2 and FIG. 3 show a top view and bottom view, respectively, of the device showing the location of the on/off power switch 16 and an arrangement of the light emitting diodes 19 arranged for multiple purposes in the housing 11.

Figure 4:
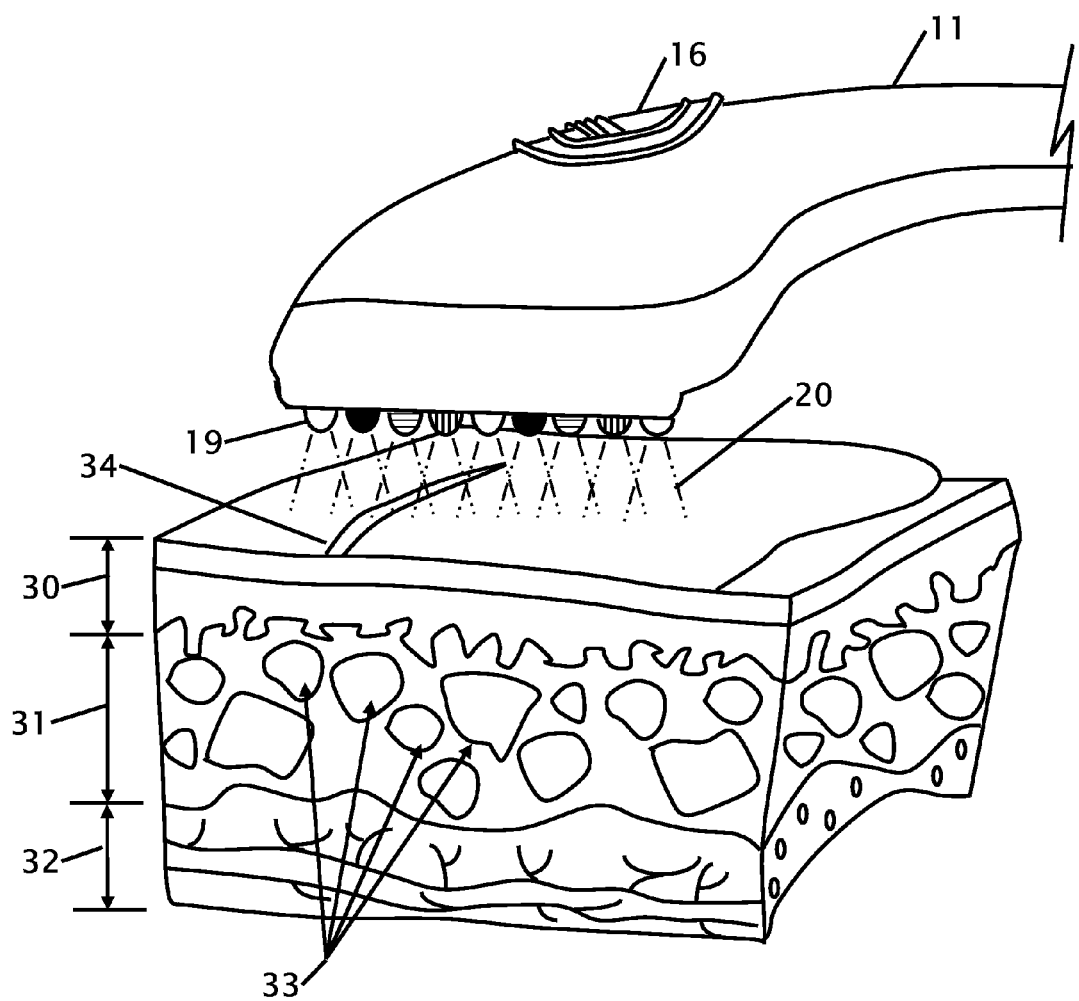
FIG. 4 shows the device in use with a cross section of skin tissue.

FIG. 4 shows the device in use with a cross section of skin tissue. The device has a housing 11 with an on-off power switch 16. LED light therapy is the use of specific types of light that give off energy that stimulates your cells, thereby increasing the production of collagen and elastin. In turn, this makes your skin firmer, less wrinkled, and younger looking. This is known as photo rejuvenation. The light emitting diodes 19 give off energy in the form of light 20. The light emitting diodes 19 are compact, durable, powerful, bright, efficient, and produce rejuvenating effects on the skin.

Skin is made up of 3 layers: the Epidermis 30, the Dermis 31 and the Subcutaneous 32. The epidermis 30 is the outer layer made up of non-living cells that form your body's protective cover. These cells are constantly being shed and replaced by new ones. The new cells are made in the lower part of the Epidermis 30. These are called Keratinocytes which produce the tough, fibrous protein called Keratin The next layer is the dermis 31. It is thicker and contains blood vessels, nerves and connective tissue. There are two main proteins in the Dermis 31 or second layer of skin. The first main protein is collagen that makes up approximately ¾ of the dermis and is made up of this protein that is responsible for the strength and plumpness of the skin. The second protein is elastin, which is responsible mainly for the elasticity of the skin.

The next layer is the subcutaneous 32, it is the layer that contains the fatty tissues and stores energy, provides warmth and a cushion etc.

People need certain wavelengths of light similar to the way plants need sunlight to thrive. Photo Rejuvenation produced by the device 11 translates the process of plant photosynthesis into the workings of human skin cells; thereby stimulating the bodies own cells to build new proteins the same way plants use chlorophyll to convert sunlight into cellular building blocks.

Skin and other body tissues have the ability to absorb light and use it as a source of energy to stimulate cellular regeneration. The light rays 20 that are emitted from the device are beneficial for your skin, as they contain no UV rays. The problem with getting these same light rays from the sun is that you also get the harmful UV rays. These harmful rays can do more damage to your skin than good. With light emitting diodes, when the correct wavelengths of light are closely and intensely flowed into the body, collagen and elastin is produced in cells called Fibroblasts 33. Inside these cells is a smaller cellular structure called Mitochondria.

Mitochondria are responsible for converting nutrients into an energy carrier known scientifically as Adenosine Triphosphate (ATP). This (ATP) fuels the cell's activities; it gives the cells the needed energy to do their job. This is the reason Mitochondria are frequently referred to as the powerhouse of the cell. The device 11 sends light rays 20 into the fibroblast cells 33, which in turn excite the mitochondria into producing in some cases up to 10 times more ATP, but usually 2 to 4 times. This fuels the cell's activities, which causes more of the needed collagen and elastin to be produced, as well as other needed materials for the skin. The light rays 20 reduce or eliminate wrinkles 34 on the epidermis 30.

Figures 5, 6:
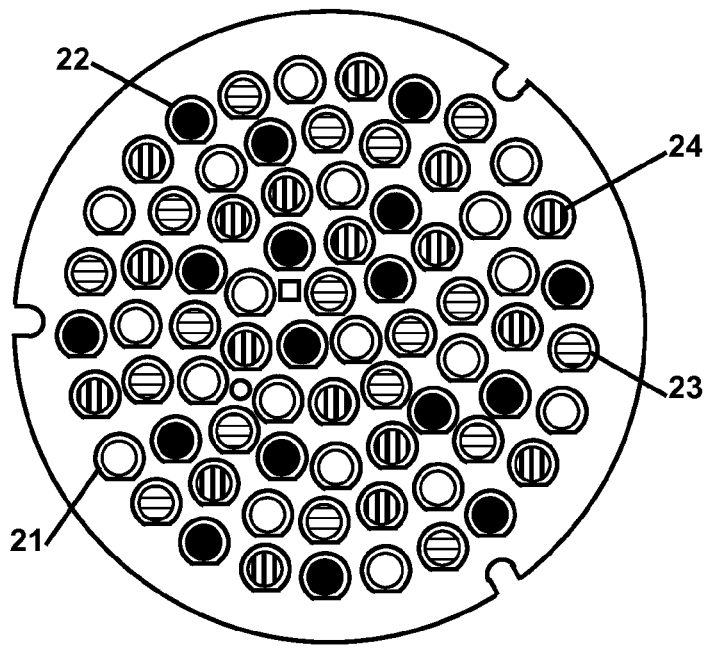
FIG. 5 is a bottom view of the device showing the arrangement of the different wavelength light emitting diodes.
FIG. 6 is a table identifying the different colored light emitting diodes for four different intended purposes.

FIG. 5 is a bottom view of the device showing the arrangement of the different wavelength light emitting diodes. Depending upon the intended purpose of the device different colored, or wavelength light emitting diodes 21-24 are used. In figure five the different colors or the array of light emitting diodes is shown. In FIG. 6 a table is shown identifying the different colored light emitting diodes 21-24 for four different intended purposes including but not limited to skin rejuvenation, reduction of rosacea, reduction of acne and therapeutic application.

Figure 7:
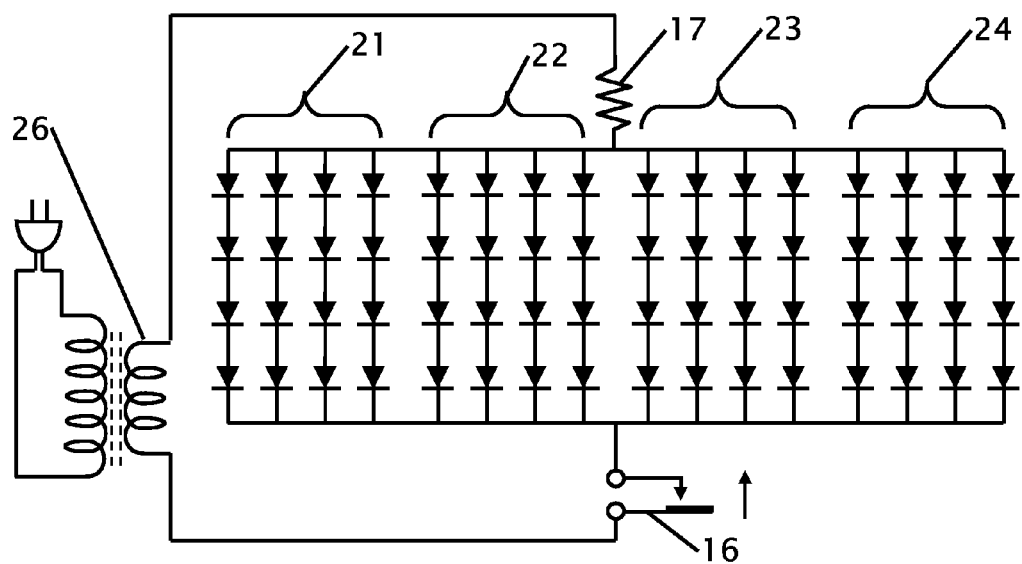
FIG. 7 shows an electrical diagram of the device.

FIG. 7 shows an electrical diagram of the device. A switch 16 connects the wall transformer power supply 26 to the remainder of the circuit. An AC to 9-12 volt DC power adapter 26 to provide operation of the light emitting diode circuits 21-24 powers the light emitting diode array. The AC to DC power adapter 26 provides the voltage and amperage required for optimal output and life of the light emitting diodes 21-24. In the preferred embodiment shown the light emitting diode array includes a plurality of diode circuits connected in parallel 21-24 with the diodes of each circuit being series connected. An electrical resistor 17 is positioned so as to current limit the current to the entire circuit board for the purpose or regulating current to the light emitting diodes and maintaining a comfortable operating temperature of the device. The effect of the light emitted is a function of each wavelength.

The value of the resistor 17 is carefully selected and tested based upon the light emitting diodes 21-24 that are selected and the operating voltage of the light emitting diodes. The selection of the resistor 17 is selected to overdrive the light emitting diodes such that they produce thermal heating. Overdriving the light emitting diodes provides a higher illumination intensity to more deeply penetrate the skin. The selection of the resistor must also be determined to minimize overheating to the skin. In the preferred embodiment the current limiting resistor is selected to cause a deliberate increase in said skin tissue temperature of between 97-106 degrees Fahrenheit when held continuously against or in close proximity to said skin tissue for a 15-minute period. A device made for anti-aging light would have a resistor with a nominal value of 2.0 to 2.8 ohms, a device made for treatment of acne would have a nominal resistor value of 1.8 to 3.0 ohms, a rosacea lamp would have a resistor valued between 1.8 and 3.2 ohms and a therapeutic light would have a nominal resistor of 6.2 to 7.5 ohms.

A therapy protocol when using the device requires about 2 to 5 minutes of exposure before relocating the device to another area of concern. This process is repeated in each area. This regimen can be performed daily until the desired appearance of the skin is achieved.

Figure 8:
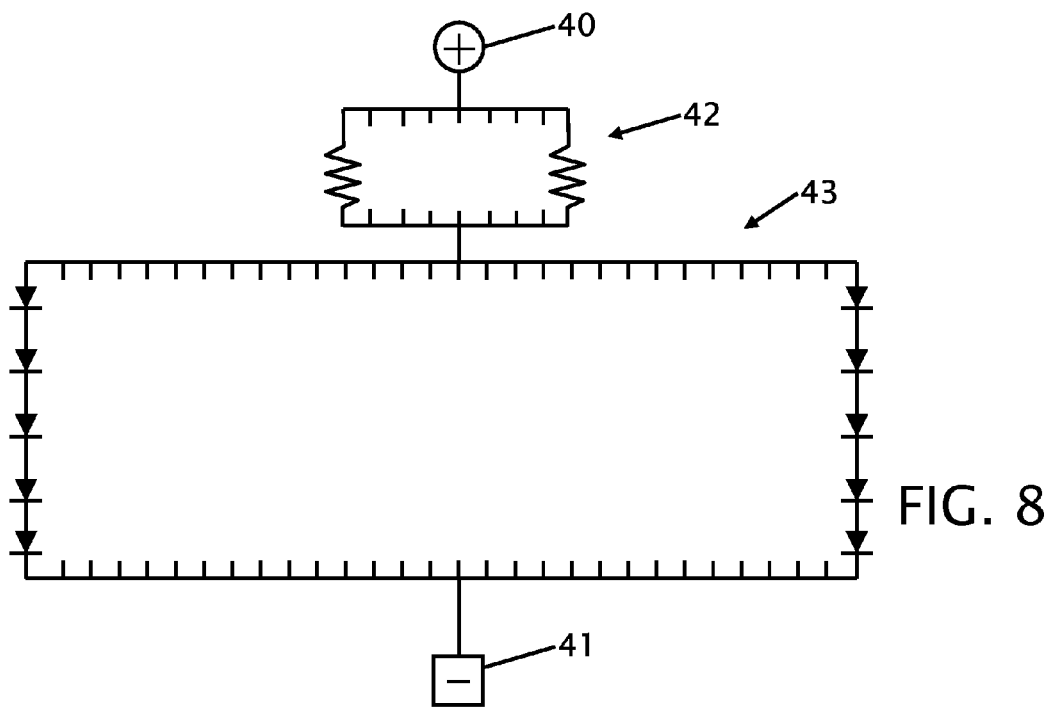
FIG. 8 shows an electrical diagram of a larger panel of light emitting diodes.
Figure 9:
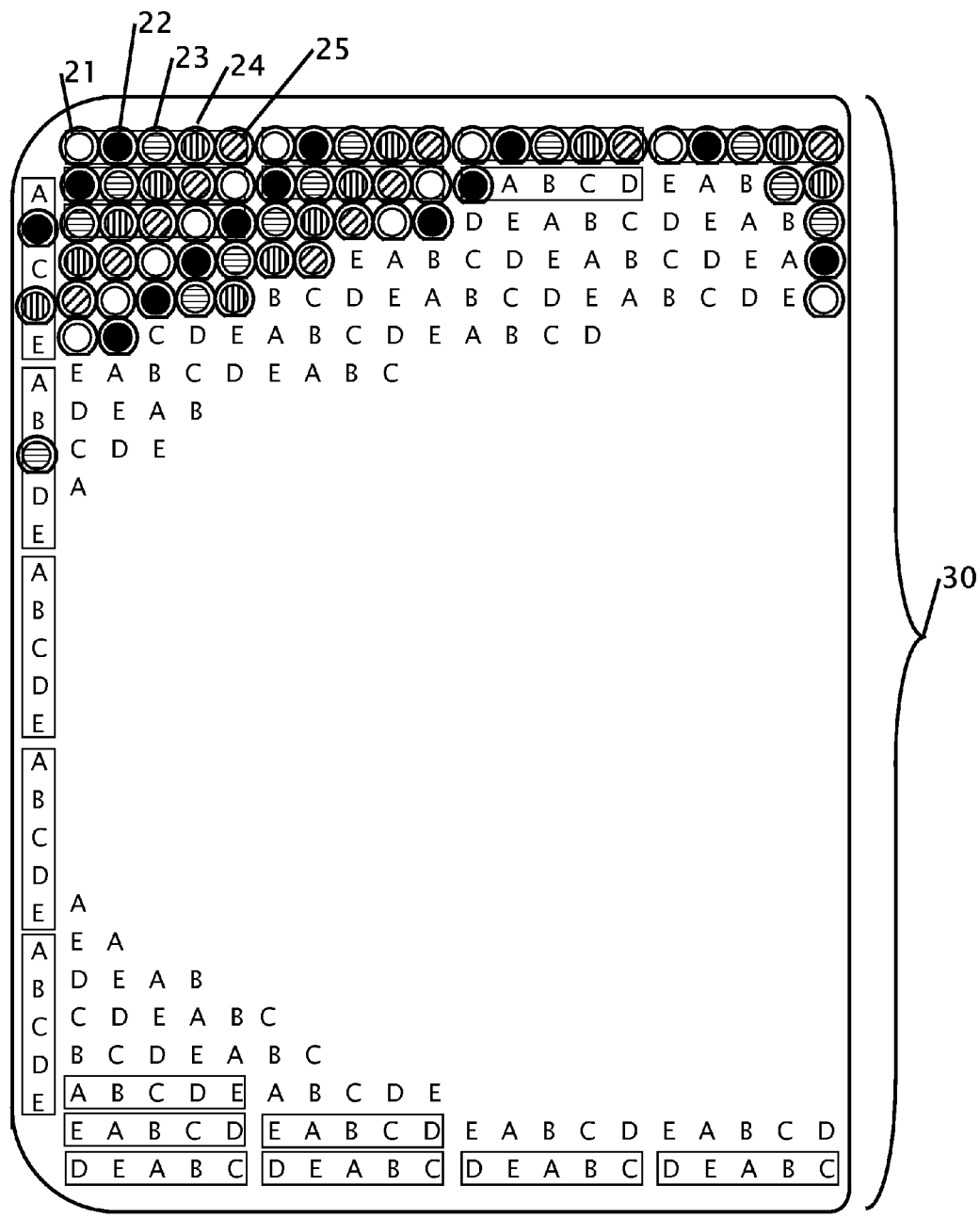
FIG. 9 shows a bottom view of the array of five different colored light emitting diodes as identified in the electrical diagram of FIG. 8.

FIG. 8 shows an electrical diagram of a larger panel of light emitting diodes and FIG. 9 shows a bottom view of the array of five different colored light emitting diodes as identified in the electrical diagram of FIG. 8. In this circuit an array of resistors 42 is used to minimize the physical thickness of the unit, but a single resistor could also be used. The resistor and light emitting diode circuit is connected to a positive terminal 40 and a negative terminal 41 from a 12 volt DC power supply of about 5.4 Amps. In one preferred embodiment the panel comprises an array 43 of five different colored or wavelength light emitting diodes with 1130 light emitting diodes 21-25. The 1130 light emitting diodes are selected from the following groups of light emitting diodes 226 (460 nm, 465 nm, 605 nm, 630 nm, 660 nm, 880 nm and 940 nm wavelength light emitting diodes) in a repeating pattern as shown in panel 30. While these quantities and wave lengths of light emitting diodes are disclosed various different ratios and wavelengths are contemplated based upon the application.

Thus, specific embodiments of a therapy system utilizing light emitting diodes as a source of bio-stimulative have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. A tissue therapy device comprising:
an enclosure;
a circuit board secured within said enclosure;
said circuit board including an array of at least three different wavelength light emitting diodes configured to provide photodynamic stimulation of a surface and underlying layers of cells of skin tissue, wherein the stimulation of cells increases production of collagen and elastin; a power jack that receives DC power and a power switch electrically connected to said
array of light emitting diodes though a single current limiting circuit;
said single current limiting circuit is one resistor;
wherein operating current of each of said different wavelength light emitting diodes is from the single current limiting circuit;
said single current limiting circuit and a voltage supplied to said power jack is selected so that at least one of said different wavelength light emitting diodes is overdriven to increase light output of said light emitting diodes beyond normal operating intensity and to further produce thermal heat from said light emitting diodes, wherein the single current limiting circuit consistently limits the current to all of the at least three different wavelength light emitting diodes to produce a skin temperate of between 97 and 106 degrees Fahrenheit from direct thermal conduction of said thermal heat from said light emitting diodes when held continuously against or in close proximity to said skin tissue for predetermined period of time; wherein the device is configured to heat the skin of a patient to between 97-106 degrees Fahrenheit, and
wherein said array of light emitting diodes is placable directly against skin tissue to produce a rise in skin temperature within a finite period of time without utilizing an optical system or any intermediary material to produce said rise in skin tissue temperature.

2. The tissue therapy device according to claim 1 wherein said circuit board is configured to operate all of said light emitting diodes with only a single positive and single negative connection from said power switch and said current limiting circuit.

3. The tissue therapy device according to claim 1 wherein all of said light emitting diodes are contained on at least one printed circuit board.

4. The tissue therapy device according to claim 3 wherein said circuit board has electrical connections for between 36 to 72 light emitting diodes.

5. The tissue therapy device according to claim 4 wherein said different wavelength light emitting diodes are placed in a repeating pattern and close proximity in a spiral array so that a skin target area receives all wavelengths simultaneously.

6. The tissue therapy device according to claim 1 wherein said current limiting resistor provides current limiting to overdrive the LED with constantly current to cause the temperature of skin tissue to increase while limiting heating of said light emitting diodes to prevent thermal damage.

7. The tissue therapy device according to claim 1 wherein said light emitting diodes are connected in groups of at least four light emitting diodes connected in series with 9-18 circuits in parallel through a single current limiting circuit.

8. The tissue therapy device according to claim 1 wherein said light emitting diodes transmit light in the wavelengths of 605 nm, 630 nm, 660 nm and 850 nm for skin rejuvenation.

9. The tissue therapy device according to claim 8 that further includes a power supply that converts wall power into 9-12 volt direct current at 300-500 mA.

10. The tissue therapy device according to claim 1 wherein said light emitting diode transmit light in the wavelengths of 465 nm, 630 nm, 660 nm and 850 nm for treatment to reduce rosacea.

11. The tissue therapy device according to claim 10 further including a power supply that converts wall power into 9-12 volt direct current at 300-500 mA.

12. The tissue therapy device according to claim 1 wherein said light emitting diodes transmit light in the wavelengths of 460 nm or, 465 nm, 660 nm and 850 nm for the purpose of the reduction of acne.

13. The tissue therapy device according to claim 12 that further including a power supply that converts wall power into 9-12 volt direct current at 300-500 mA.

14. The tissue therapy device according to claim 1 wherein said light emitting diodes transmit light in the wavelengths of 630 nm, 660 nm, 850 nm and 940 nm for the purpose of therapeutic applications.

15. The tissue therapy device according to claim 14 further including a power supply that converts wall power into 9-12 volt direct current at 300-500 mA.

16. The tissue therapy device according to claim 1 that uses at least five different wavelength light emitting diodes placed in at least 113 parallel circuits using a repeating pattern of the different wavelengths of said light emitting diodes.

\* \* \* \* \*

UNITED STATES PATENT AND TRADEMARK OFFICE
CERTIFICATE OF CORRECTION

| | | |
|---|---|---|
| PATENT NO. | : 9,079,022 B2 | Page 1 of 3 |
| APPLICATION NO. | : 12/205199 | |
| DATED | : July 14, 2015 | |
| INVENTOR(S) | : Baird et al. | |

It is certified that error appears in the above-identified patent and that said Letters Patent is hereby corrected as shown below:

*Title page, Abstract, line 8;

"or" should be --of--.

In the specification

*Col. 1, line 37;

"patient's" should be --patients--.

*Col. 1, line 46;

"Nonmonochromatic" should be --Non-monochromatic--.

*Col. 1, line 50;

"With" should be --with--.

*Col. 1, line 60;

"TO" should be --to--.

*Col. 2, line 23;

"LED's" should be --LEDs--.

*Col. 2, line 29;

"LED's" should be --LEDs--.

*Col. 2, line 39;

"LED's" should be --LEDs--.

*Col. 2, line 40;

"LED's" should be --LEDs--.

*Col. 2, lines 44-45;

"LED's" should be --LEDs-- (both occurrences).

*Col. 2, line 48;

"LED's" should be --LEDs--.

Signed and Sealed this
Twenty-second Day of December, 2015

Michelle K. Lee
*Director of the United States Patent and Trademark Office*

CERTIFICATE OF CORRECTION (continued)
U.S. Pat. No. 9,079,022 B2

*Col. 2, line 50;
"LED's" should be --LEDs--.

*Col. 2, line 56;
"comprises" should be --comprise--.

*Col. 3, line 13;
"LED's" should be --LEDs--.

*Col. 3, line 16;
"LED's" should be --LEDs--.

*Col. 3, line 40;
"cross sectional" should be --cross-sectional--.

*Col. 3, line 40;
"hand held" should be --handheld--.

*Col. 3, line 61;
"cross sectional" should be --cross-sectional--.

*Col. 3, line 61;
"hand held" should be --handheld--.

*Col. 3, line 66;
After "wavelengths" insert --:--.

*Col. 4, line 8;
After "volt" insert --,--.

*Col. 4, line 15;
"cross sectional" should be --cross-sectional--.

*Col. 4, line 31;
"photo rejuvenation" should be --photo-rejuvenation--.

*Col. 4, line 41;
After "Keratin" insert --.--.

*Col. 4, line 54;
"Photo Rejuvenation" should be --Photo-rejuvenation--.

*Col. 4, line 57;
"bodies" should be --body's--.

*Col. 5, line 20;
"or" should be --of--.

*Col. 5, line 37;
"or" should be --of--.

CERTIFICATE OF CORRECTION (continued)
U.S. Pat. No. 9,079,022 B2

*Col. 5, line 57;

"valued" should be --value--.

*Col. 5, line 58;

After "resistor" insert --value--.

*Col. 6, line 13;

"wave lengths" should be --wavelengths--.

*Col. 6, line 18;

"bio-stimulative" should be --bio-stimulation--.

In the claims

*Col. 6, claim 1, line 36;

and "though" should be --through--.

*Col. 6, claim 1, line 54;

After "for" insert --a--.

*Col. 6, claim 1, line 54;

Insert new paragraph after "time;".

*Col. 6, claim 1, line 57;

"," should be --;--.

*Col. 7, claim 6, line 14;

"constantly" should be --constant--.

*Col. 8, claim 10, line 2;

"diode" should be --diodes--.

*Col. 8, claim 12, line 10;

Delete "or".

*Col. 8, claim 13, line 12;

"including" should be --includes--.